United States Patent [19]

O'Brien

[11] 4,383,842
[45] May 17, 1983

[54] DISTILLATIVE SEPARATION OF METHANE AND CARBON DIOXIDE

[75] Inventor: John V. O'Brien, Shrewsbury, Mass.

[73] Assignee: Koch Process Systems, Inc., Westborough, Mass.

[21] Appl. No.: 307,672

[22] Filed: Oct. 1, 1981

[51] Int. Cl.³ .............................................. F25J 3/00
[52] U.S. Cl. ........................................... 62/20; 62/28
[58] Field of Search ................... 62/28, 27, 24, 23, 17, 62/20

[56] References Cited

U.S. PATENT DOCUMENTS

| | | | |
|---|---|---|---|
| 3,683,634 | 8/1972 | Streich | 62/28 |
| 4,149,864 | 4/1979 | Eakman et al. | 62/28 |
| 4,284,423 | 8/1981 | Eakman et al. | 62/28 |
| 4,318,723 | 3/1982 | Holmes et al. | 62/28 |

*Primary Examiner*—Norman Yudkoff
*Attorney, Agent, or Firm*—Hamilton, Brook, Smith & Reynolds

[57] ABSTRACT

An improvement in a Ryan/Holmes separation of methane from carbon dioxide is disclosed wherein the upper portion of a distillation column is operated at temperatures above the triple point of carbon dioxide, i.e., $-70°$ F., while still effectuating a separation of methane from carbon dioxide. This is achieved by increasing the amount of non-polar liquid agent added to the condenser of the column to an amount sufficient to maintain the condenser and all portions of the column at such temperatures.

20 Claims, 1 Drawing Figure

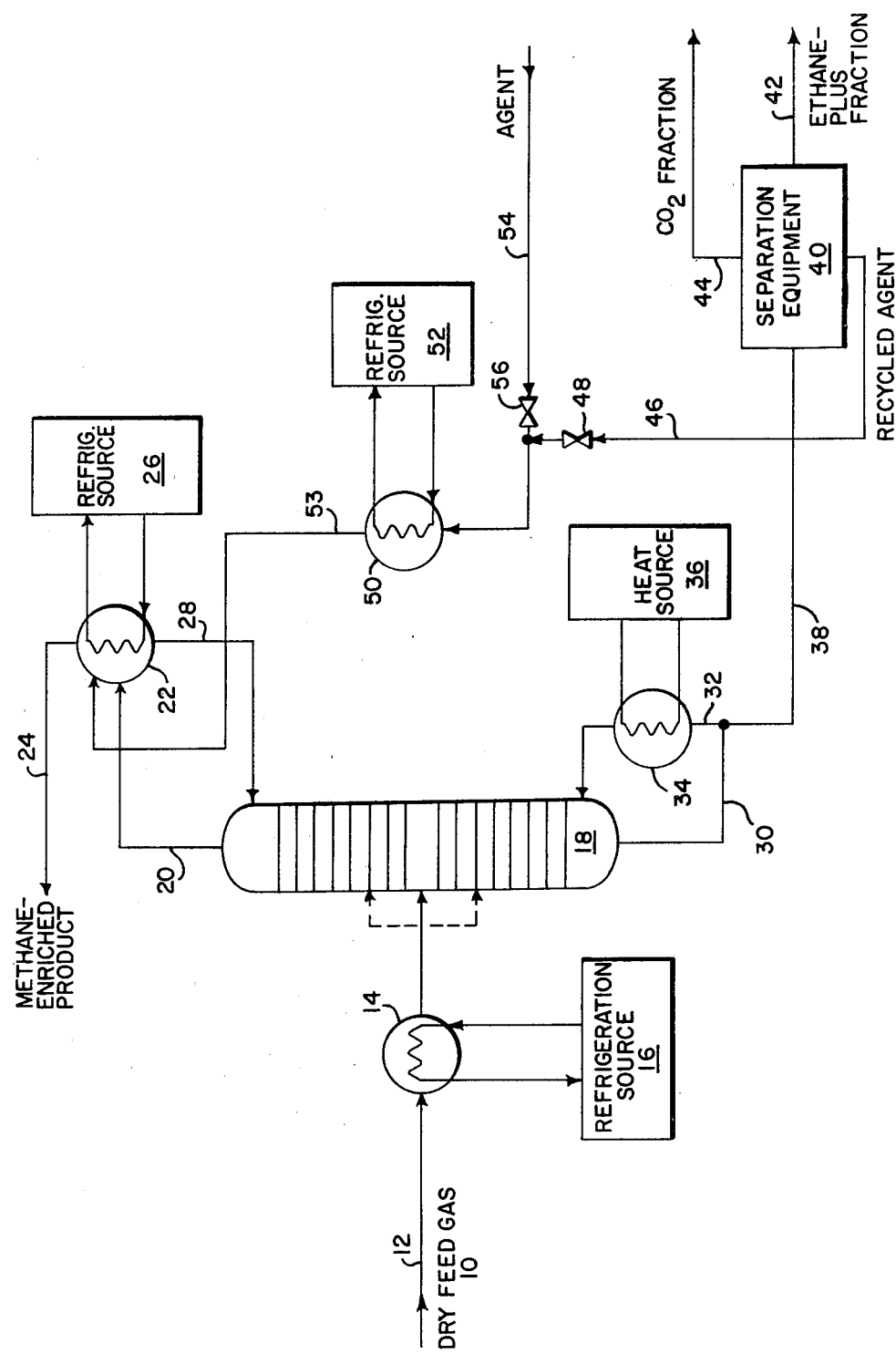

DISTILLATIVE SEPARATION OF METHANE AND CARBON DIOXIDE

DESCRIPTION

1. Technical Field

This invention is in the field of distillation.

2. Background Art

There are many situations in which it is desirable to separate methane from carbon dioxide. For example, gas streams obtained from natural gas wells often contain relatively high amounts of carbon dioxide which lowers the heating value of the gas and are highly corrosive. In such situations, carbon dioxide must be removed from the gas stream in order to meet the carbon dioxide specification for saleable gas products. Additionally, carbon dioxide usually must be separated from gas mixtures caused by injecting carbon dioxide-containing gases into oil wells for enhanced oil recovery.

Generally, the processes developed for separating methane and carbon dioxide can be classified into certain broad categories. These include carbon dioxide adsorption by solids, carbon dioxide adsorption by chemical solvents, carbon dioxide absorption by physical solvents and distillative separations at relatively low temperatures. Distillative separations offer many advantages and are possible because the relative volatility of methane to carbon dioxide is reasonably high. However, the behavior of methane/carbon dioxide systems has often prevented such distillative separations from becoming commercially practical for separations requiring substantially complete carbon dioxide separation from high-carbon dioxide content gases. This is because solid carbon dioxide coexists with a vapor and liquid mixture of methane and carbon dioxide at certain compositions, temperatures and pressures encountered in distillative separations. At these conditions, carbon dioxide freezes out of solution and would potentially plug up a distillation column as well as other equipment thereby making the process inoperative. On the other hand, at higher pressures, where carbon dioxide does not freeze out, methane-rich mixtures become supercritical fluids not subject to further purification of methane by distillation. Thus, raising the pressure in a column above that where carbon dioxide freeze out occurs is not usually a viable alternative to achieving further methane separation.

In a copending application, Ser. No. 94,226, filed Aug. 14, 1979 in the names of Arthur S. Holmes and James M. Ryan, a process which has become known as the "Ryan/Holmes" process is described. The Ryan/Holmes process can be employed to separate a feed gas mixture containing methane and carbon dioxide in a distillation column into a methane overhead product substantially free of carbon dioxide and a carbon dioxide bottoms product substantially free of methane. Unlike many other prior distillative separations, the Ryan/Holmes process involves the operation of the distillation column at temperatures, compositions and pressures which produce a solids potential zone for carbon dioxide within the tower. The term "solids potential zone" is employed with the Ryan/Holmes process because, although conditions in the tower are such that carbon dioxide solids would normally occur, the Ryan/Holmes process prevents actual solids formation from occurring. This is achieved by introducing into the upper portion of the distillation column an agent for preventing acid gas solids. The agent can be an external additive, or in the alternative, can be one or more recycled components from the bottoms product taken from the distillation column. A more detailed description of the use of the Ryan/Holmes process for separating methane from carbon dioxide, as well as the prior art cryogenic distillative separations of methane and carbon dioxide, can be found in Ser. No. 94,226, the teachings of which are hereby incorporated by reference.

In a typical separation of methane from carbon dioxide employing the Ryan/Holmes process, the temperature levels in the overhead condenser of the distillation column have heretofore run in the order of about $-125°$ F. Such low temperatures are typically achieved by employing a cascaded ethylene-propane refrigeration system. Because of the low temperatures at the overhead, and operating column pressures which are typically 500 psia or higher, the distillation column and associated equipment was typically fabricated from stainless steel.

DISCLOSURE OF THE INVENTION

This invention concerns an improved low temperature method and apparatus for the distillative separation of methane and carbon dioxide. In particular, this invention relates to an improvement in a Ryan/Holmes process for separating methane from carbon dioxide.

It has now been unexpectedly discovered by Applicant that a Ryan/Holmes process for separating methane and carbon dioxide can be carried out employing much warmer temperatures in the upper portion of the distillation column than heretofore believed possible. In this improved distillative process, the upper portion of the distillation column in a Ryan/Holmes process is operated above the triple point of carbon dioxide, i.e., above about $-70°$ F. As long as the temperature is maintained above the triple point of carbon dioxide, formation of carbon dioxide solids does not occur.

In this improved distillative process, a feed stream containing methane and carbon dioxide is introduced into a distillation column. Prior to introduction, the feed stream may be cooled but preferably should not be cooled below the triple point of carbon dioxide to avoid solids formation. The distillation column is provided with sufficient heat at its bottom to produce a bottoms product enriched in carbon dioxide. Overhead, a stream enriched in methane is withdrawn and at least a portion of the withdrawn overhead stream is condensed. A condensed portion of overhead stream serves as reflux to the tower so that the condensed portion must be sufficient to provide a column overhead enriched in methane.

In a manner superficially similar to a typical Ryan/Holmes process for separating methane from carbon dioxide, a non-polar agent miscible with methane is introduced into the condenser of the distillation column. However, in the improved separation described herein, the agent must be maintained at a temperature above the triple point of carbon dioxide. There must also be sufficient quantity of agent introduced into the upper portion of the column to maintain the temperature at all locations in the upper portion of the column above the triple point of carbon dioxide. Typically, this means that much larger amounts of agent are introduced into the condenser than have heretofore been suggested for use in the Ryan/Holmes separation of methane from carbon dioxide.

That portion of withdrawn overhead stream not employed as reflux is withdrawn as overhead product enriched in methane.

In summary, it can be seen that in this improvement of a Ryan/Holmes distillative separation of methane from carbon dioxide, the column is operated much warmer than had heretofore been suggested. This is achieved by introducing a sufficient quantity of nonpolar agent to maintain temperatures in the upper portion of the column above the triple point of carbon dioxide. Preferably, the feed is also introduced into the column at a temperature above the triple point of carbon dioxide.

Thus, the improved Ryan/Holmes process for separating methane from carbon dioxide described herein offers advantages over the typical Ryan/Holmes separation previously proposed. Among the significant advantages is the elimination of a requirement for a refrigeration system capable of chilling the upper portions of a distillation column to temperatures significantly below the triple point of carbon dioxide. It has been found, for example, that a propane refrigeration system can be employed instead of the more complex and costly cascaded ethylene/propane refrigeration systems typically previously employed.

The use of warmer temperatures in the column also means that the column and associated items can often be made from carbon steel rather than from stainless steel.

It has also been found that higher operating pressures can be employed with this improved Ryan/Holmes process compared to previous Ryan/Holmes separations of methane from carbon dioxide.

Further, the process can be readily adapted to produce pipeline quality gas ($<2\%$ $CO_2$) or LNG quality gas ($<50$ ppm $CO_2$) and the process can handle low or high carbon dioxide content feeds.

It is still yet an additional advantage that the dehydration requirement of the feed gas is not as severe as with the lower temperature Ryan/Holmes process. The water dew point can match the lowest refrigerant temperature (e.g., $-70°$ F. or $-40°$ F. or warmer). Thus, glycol dehydration can often be employed instead of molecular sieve bed systems.

Also, the ability to control the column overhead temperature at different levels, independently of the $CO_2$ content, enables the designer to control the hydrocarbon dew point of the product methane stream.

Features of the process shared with the lower temperature Ryan/Holmes process include: capability of reducing the $H_2S$ content of feed and total sulfur to below ¼ grain/100 SCF and the capability for complete extraction of the ethane from the feed. Finally, carbonyl sulfide and mercaptans can be removed from feed gases in the course of removing carbon dioxide.

BRIEF DESCRIPTION OF THE DRAWING

The Figure is a schematic flow diagram illustrating the improved Ryan/Holmes distillative process for separating methane from carbon dioxide described herein.

BEST MODE OF CARRYING OUT THE INVENTION

This invention will now be described with more specific detail with regard to the Figure.

In the Figure, it can be seen that dry feed gas 10, containing a mixture of methane and carbon dioxide, and usually other components such as nitrogen and higher alkanes, enters in inlet feed line 12. The feed gas is cooled in heat exchanger 14 which receives refrigeration from refrigeration source 16. Feed gas exiting from exchanger 14 should preferably have a temperature above the triple point of carbon dioxide since the column is run at such temperatures.

Thereafter, cooled feed is introduced into one or more of the feed points in distillation column 18. Distillation column 18 contains a number of vapor-liquid contact devices, such as trays or packing, with the exact number of contact stages depending upon the required operating conditions, of course. Overhead is withdrawn in overhead line 20 and passed to condenser 22. Methane-enriched product is withdrawn in line 24.

Condenser 22 receives refrigeration from refrigeration source 26 sufficient to condense at least a portion of overhead to provide reflux in line 28 to tower 18. Since the upper portion of tower 18 is maintained above the triple point of carbon dioxide in this separation, refrigeration source 26 and can be a propane refrigeration system rather than a cascaded ethylene/propane system often employed if temperatures of about $-130°$ to $-140°$ F. were required. Other common refrigeration systems capable of condensing a portion of the overhead stream withdrawn in line 20, such as Freon®, ammonia, propylene, carbon dioxide, etc., might also be employed. The requirement is, of course, to maintain the temperature at a temperature no lower than the triplet point of carbon dioxide, which is about $-70°$ F. Preferably, the temperature is maintained even higher, such as above about $-40°$ F.

Bottoms exits from column 18 through line 30 and part of the bottom is recycled to column 18 via line 32 which passes through reboiler heat exchange 34 supplied with heat energy from heat source 36. This provides vaporization heat to the bottom of column 18. The balance of the bottoms passes through line 38 to further separation equipment 40 for separating out other fractions, such as an ethane plus fraction separated and collected through line 42. A carbon dioxide fraction is extracted through line 44.

It is sometimes possible to separate non-polar liquid agent from bottoms, such as natural gas liquids (NGL), which is shown as recycled agent. The recycled agent exits from the separation equipment 40 in line 46 and valve 48 regulates the flow of such recycled agent through heat exchanger 50 cooled by refrigeration source 52, back to condenser 22. Refrigeration source 52 need only be sufficient to cool the agent to a point above the triple point of carbon dioxide. Recycled, cooled agent exiting from heat exchanger 50 flows in line 53 into condenser 22. It may also be added to column 18 at additional points, if desired.

In another alternative embodiment, a non-polar agent can be externally added. For example, agent can be added externally via line 54 into heat exchanger 50, in which case the flow is controlled by valve 56.

Typical agents which can be employed include ethane, propane, butane, pentane and mixtures thereof. In general, non-polar materials which are miscible with methane, such as $C_3$–$C_6$ alkanes, are preferred agents because they are typically present in feed gases, are easy to separate and recycle, and seem to have a very beneficial effect on raising the operating temperature in the upper portions of the distillation column. Certain natural gas liquids (NGL) contain such alkanes and can often be separated from the bottoms product in conventional separation equipment. Thus, these NGL or components thereof can be conveniently recycled. It is also clear that agents need not be pure materials and may comprise mixtures of components.

The amount of non-polar agent added will depend upon factors such as the composition of the feed, operating pressure, throughput of the column, desired purity of overhead methane, etc. In general, larger amounts of agent are employed than had heretofore been suggested for use in Ryan/Holmes separations of methane from carbon dioxide. More specifically, it has been found that an amount of non-polar agent of more than one mole per mole of methane in the feed stream can be employed, and more preferably from about 2 to about 10 moles per mole of methane in the feed.

Since the column is operated under conditions which do not approach conditions under which carbon dioxide would freeze, a very wide range of carbon dioxide-content feed gases can be employed. Feeds can contain virtually any amount of carbon dioxide and the only limitation on use of this process to reduce the carbon dioxide is one of economic practicality. It is, of course, a particularly advantageous process for feeds containing high amounts (e.g., >50%) of carbon dioxide. On the other hand, the process can be employed in the production of pipeline quality gas (i.e., <2-3% $CO_2$) and even LNG quality gas (i.e., <50 ppm $CO_2$).

The pressure in the distillation column is maintained below the critical pressure of any mixture therein so that a distillative separation can be performed. However, the addition of large amounts of non-polar agent typically raises the critical pressure of the system, which means that a relatively wide range of pressures are suitable. For example, it has been typical with a Ryan/Holmes separation of methane from carbon dioxide to employ pressures in the range of above 600–700 psig, but operating the column at warmer temperatures as described herein often means that pressures of well over 1000 psig can be employed.

In order to further describe this invention, a number of computer simulations will now be described. These were run using a plate-to-plate column calculation program to simulate conditions within the distillation column for certain given or desired operating conditions. The program employed was the PROCESS SM Simulation Program from Simulation Sciences, Inc., Fullerton, Calif., version 1080. Vapor-liquid equilibria and thermodynamic data for methane/carbon dioxide systems were calculated based upon the Peng-Robinson equation of state. Product specifications were established as 0.5% methane in the bottoms product, 2% carbon dioxide in the overhead, and less than 3.8 ppm $H_2S$ (¼ grain/100 SCF) in the overhead. The feed and additive employed are presented below in Table I:

TABLE I

| Component | Composition, Mole Percent | |
|---|---|---|
| | Feed Gas | Agent |
| Hydrogen Sulfide | 0.12 | 0 |
| Nitrogen | 0.07 | 0 |
| Carbon Dioxide | 87.09 | 0 |
| Methane | 5.03 | 0 |
| Ethane | 2.61 | 0 |
| Propane | 2.27 | 0.5 |
| Isobutane | 0.39 | 2.90 |
| Normal Butane | 1.13 | 16.39 |
| Isopentane | 0.38 | 14.95 |
| Normal Pentane | 0.48 | 22.44 |
| Normal Hexane | 0.32 | 28.21 |
| Normal Heptane | 0.11 | 14.61 |

TABLE I-continued

| Component | Composition, Mole Percent | |
|---|---|---|
| | Feed Gas | Agent |
| | 100.00 | 100.00 |

This NGL mix employed as non-polar agent miscible with methane was separated out from the bottoms product of the demethanizer column in subsequent columns.

The results of the computer simulations are presented in Table II.

TABLE II

| | | | | |
|---|---|---|---|---|
| Column Pressure, psia | 500 | 500 | 500 | 500 |
| Feed Rate, lb.moles/hr | 7996 | 7996 | 7996 | 7996 |
| Additive Rate, lb.moles/hr | 750 | 900 | 1250 | 1400 |
| Feed & Additive Temp, °F. | −35 | −35 | −35 | −35 |
| Ratio Additive/Methane in Feed, moles/mole | 1.9 | 2.5 | 3.2 | 3.53 |
| Number of Theoretical Trays | 17 | 17 | 17 | 17 |
| Feed Tray | 11 | 11 | 11 | 11 |
| Overhead Product | | | | |
| Temperature, °F. | −83.3 | −70.0 | −44.9 | −36.5 |
| Condenser Duty, mmBtu/hr | 3.08 | 2.78 | 2.03 | 1.68 |
| Rate, lb.moles/hr | 367.4 | 366.9 | 365.9 | 365.5 |
| Composition, mole % | | | | |
| $H_2S$ | 1.2 ppm | 1.7 ppm | 2.8 ppm | 3.3 ppm |
| $N_2$ | 1.52 | 1.52 | 1.53 | 1.53 |
| $CO_2$ | 2.00 | 2.00 | 2.00 | 2.00 |
| $CH_4$ | 96.35 | 96.28 | 96.05 | 95.95 |
| $C_2H_6$ | 16 ppm | 21 ppm | 33 ppm | 38 ppm |
| $C_3H_8$ | 0.02 | 0.03 | 0.05 | 0.05 |
| $iC_4H_{10}$ | 0.02 | 0.03 | 0.06 | 0.07 |
| $nC_4H_{10}$ | 0.07 | 0.11 | 0.23 | 0.28 |
| $iC_5H_{12}$ | 0.01 | 0.02 | 0.04 | 0.05 |
| $nC_5H_{12}$ | 0.01 | 0.02 | 0.04 | 0.05 |
| $nC_5H_{14}$ | 20 ppm | 34 ppm | 84 ppm | 0.01 |
| $nC_6H_{16}$ | 6 ppm | 10 ppm | 28 ppm | 39 ppm |
| Bottoms Product | | | | |
| Temperature, °F. | 37.5 | 38.3 | 40.1 | 40.8 |
| Reboiler Duty, mmBtu/hr | 19.63 | 20.13 | 21.11 | 21.48 |
| Methane Content, Mole Percent | 0.5 | 0.5 | 0.5 | 0.5 |

In the first column of Table I, it can be seen that 750 moles per hour of agent was insufficient to maintain the upper portion of the tower above the triple point of carbon dioxide. Note, the overhead temperature of −83° F. Hence, a solids potential zone formed and had an approach to freezing of approximately 50° F. This is, then, an example of a typical Ryan/Holmes process for separating methane from carbon dioxide with the column being run at colder temperatures.

Subsequent runs, where the amount of agent was increased to 900 mph or more of agent, brought the temperature in the overhead portion of the column up to the triple point or warmer. The increase in temperature is due to increased amounts of butane in the condenser.

Thus, the increased amounts of agent raise the column temperature to the range where carbon dioxide solids formation is not a concern. Surprisingly, very effective separations of methane from carbon dioxide can be achieved at these warmer temperatures with the use of relatively large amounts of agent compared to amounts previously employed in Ryan/Holmes separations.

The improved Ryan/Holmes process can also be used to reduce the $CO_2$ content of a methane-rich stream to an adequate level for further lower temperature processing, such as the liquefaction of natural gas. To illustrate this, the results of computer simulations are presented in Tables III and IV illustrating how the $CO_2$ content of the methane is reduced to 50 ppm, while the condenser temperature is controlled above the $CO_2$ triple point. Note also the $H_2S$ content of the methane stream is below 3.8 ppm and the ethane extraction from the feed is 100%.

TABLE III

|  | Composition, Mole Percent | |
| --- | --- | --- |
|  | Feed Gas | Agent |
| $H_2S$ | 0.40 | 0.0015 |
| $N_2$ | 0.25 | 0 |
| $CO_2$ | 59.29 | 0 |
| $CH_4$ | 17.19 | 0 |
| $C_2H_6$ | 8.88 | 0 |
| $C_3H_8$ | 7.47 | 0.9985 |
| $iC_4H_{10}$ | 1.21 | 20.00 |
| $nC_4H_{10}$ | 3.31 | 40.00 |
| $iC_5H_{12}$ | 0.86 | 15.00 |
| $nC_5H_{12}$ | 0.91 | 15.00 |
| $nC_6H_{14}$ | 0.21 | 7.00 |
| $nC_7H_{16}$ | 0.02 | 2.00 |
|  | 100.00 | 100.00 |

TABLE IV

| Column Pressure, psia | 500 | 500 |
| --- | --- | --- |
| Feed Rate, lb. moles/hr | 1211 | 1211 |
| Additive Rate, lb. moles/hr | 650 | 900 |
| Feed and Additive Temp, °F. | −35 | −35 |
| Ratio Additive/Methane in Feed, moles/mole | 3.1 | 4.3 |
| Number of Theoretical Trays | 17 | 17 |
| Overhead Product | | |
| Temperature, °F. | −73.5 | −61.4 |
| Condenser Duty, mmBtu/hr | 1.80 | 1.94 |
| Rate, lb. moles/hr | 196.9 | 197.2 |
| Composition, Mole % | | |
| $H_2S$ | 1.6 ppm | 2.1 ppm |
| $N_2$ | 1.52 | 1.52 |
| $CO_2$ | 50 ppm | 50 ppm |
| $CH_4$ | 98.09 | 97.94 |
| $C_2H_6$ | 0 | 0 |
| $C_3H_8$ | 0.02 | 0.03 |
| $iC_4H_{10}$ | 0.15 | 0.21 |
| $nC_4H_{10}$ | 0.17 | 0.25 |
| $iC_5H_{12}$ | 0.02 | 0.03 |
| $nC_5H_{12}$ | 0.01 | 0.02 |
| $nC_6H_{14}$ | 13 ppm | 21 ppm |
| $nC_7H_{16}$ | 1 ppm | 1 ppm |
| Bottoms Product | | |
| Temperature, °F. | 69.8 | 83.7 |
| Reboiler Duty | 6.76 | 8.57 |
| Methane Content, lb. moles/hr | 15 | 15 |

Industrial Applicability

This invention is useful in the distillative separation of methane from carbon dioxide.

Equivalents

Those skilled in the art will also recognize, or be able to determine using no more than routine experimentation, equivalents to the specific embodiments described herein.

I claim:

1. A method of distillatively separating a feed stream containing methane and carbon dioxide into an overhead product enriched in methane and a bottoms product enriched in carbon dioxide, comprising:
    (a) introducing said feed stream into a distillation column;
    (b) providing sufficient heat to the bottom of said distillation column to provide a bottom product enriched in carbon dioxide with respect to methane and carbon dioxide in the feed stream;
    (c) withdrawing an overhead stream from the top of said column;
    (d) condensing at least a portion of said overhead stream for reflux in an overhead condenser at a temperature above the triple point of carbon dioxide and directing said condensed portion of overhead back to said column as reflux, said condensed portion being sufficient to provide a column overhead enriched in methane;
    (e) introducing a liquid nonpolar agent miscible with methane into the condenser of said distillation in an amount of from about 2 to about 10 moles of agent per mole of methane in the feed stream and sufficient to maintain the temperature in the condenser and at all locations within the distillation column above the triple point of carbon dioxide;
    (f) withdrawing that portion of overhead stream not employed as reflux as overhead product enriched in methane; and
    (g) withdrawing bottoms product enriched in carbon dioxide.

2. A method of claim 1 wherein said agent comprises natural gas liquids.

3. A method of claim 1 wherein said agent comprises ethane, propane, butane, pentane or mixtures thereof.

4. A method of claim 1 wherein said agent comprises butane.

5. A method of claims 1, 3 or 4, wherein said agent is separated from the bottoms product from said distillation column and recycled to said column.

6. A method of claim 5 wherein the temperature in said condenser is maintained above about −40° F.

7. A method of claim 1 wherein the temperature in said condenser is maintained above about −40° F.

8. A method of claim 1 wherein said feed stream contains more than about 50 mole percent carbon dioxide.

9. A method of claim 1 wherein said feed stream is cooled prior to introduction to the distillation column to a temperature no lower than the triple point of carbon dioxide.

10. A method of claim 1 wherein said overhead stream contains less than about 3 mole percent carbon dioxide.

11. A method of claim 1 wherein said overhead stream contains less than about 50 ppm carbon dioxide.

12. A method of claim 1 wherein said feed stream is dehydrated employing glycol dehydration.

13. A method of claim 1 which includes employing a propane refrigeration system to chill the upper portion of the distillation column to above the triple point of carbon dioxide.

14. In a distillative separation wherein a feed stream containing methane and carbon dioxide is introduced into a distillation column and separated therein into an overhead product enriched in methane and a bottoms product enriched in carbon dioxide with respect to methane and carbon dioxide in said feed stream including withdrawing an overhead stream, condensing at least a portion thereof in a condenser, and directing said condensed portion back to the upper portion of said distillation column as reflux and wherein a nonpolar liquid agent comprising butane miscible with methane is also introduced into the condenser of said distillation column:

the improvement wherein the temperature is maintained in said condenser and at all points in said column above about −70° F. by providing an amount of from about 2 to about 10 moles of agent per mole of methane in the feed stream.

15. A method of distillatively separating a feed gas containing methane and carbon dioxide, comprising:
(a) drying said feed gas;
(b) cooling said dried feed gas to a temperature no lower than the triple point of carbon dioxide;
(c) introducing said dried, cooled feed gas into a distillation column;
(d) withdrawing a bottoms stream from said distillation column;
(e) heating a portion of said withdrawn bottoms stream and returning said heated portion to said distillation column to provide sufficient heat to provide a bottoms product enriched in carbon dioxide with respect to the feed and based upon a binary of methane and carbon dioxide;
(f) withdrawing an overhead stream from the top of said column, said overhead stream being enriched in methane;
(g) passing said overhead stream enriched in methane to an overhead condenser supplied with a source of refrigeration sufficient to condense a portion of said overhead stream, said condensed portion being returned to said column as reflux;
(h) passing the balance of withdrawn bottoms product to separation equipment for separating out a carbon dioxide fraction, an ethane-plus fraction, and agent for recycling to said distillation column;
(i) passing said agent for recycling through a cooler provided with refrigeration sufficient to cool said recycled agent to a temperature no lower than the triple point of carbon dioxide;
(j) introducing said cooled, recycled liquid agent into the overhead condenser in an amount of from about 2 to about 10 moles of agent per mole of methane in the feed stream and sufficient to maintain the temperature in the condenser and at all locations within the distillation column above the triple point of carbon dioxide; and
(k) withdrawing that portion of overhead not employed as reflux as overhead product enriched in methane.

16. A method of claim 15 wherein said agent comprises butane.

17. A method of claim 15 wherein the temperature in said condenser is maintained above about −40° F.

18. A method of claim 15 wherein said feed stream contains more than about 50 mole percent carbon dioxide.

19. A method of claim 15 wherein said overhead stream contains less than about 2 mole percent carbon dioxide.

20. A method of claim 15 wherein said overhead stream contains less than about 50 ppm carbon dioxide.

* * * * *